United States Patent [19]
Tanaka et al.

[11] Patent Number: 5,122,451
[45] Date of Patent: Jun. 16, 1992

[54] DRY LIQUID ANALYSIS ELEMENT

[75] Inventors: Mitsutoshi Tanaka; Niroyuki Hosoi; Teppei Ikeda; Shigeru Nagatomo, all of Saitama, Japan

[73] Assignee: Fuji Photo Film Ltd., Kanagawa, Japan

[21] Appl. No.: 286,359

[22] Filed: Dec. 19, 1988

[30] Foreign Application Priority Data

Dec. 18, 1987 [JP] Japan ............... 62-320709
Jan. 19, 1988 [JP] Japan ............... 63-9046

[51] Int. Cl.$^5$ ............... C12Q 1/00; G01N 31/22
[52] U.S. Cl. ............... 435/74; 422/56; 422/57; 422/58; 435/805; 435/970; 436/66; 436/71; 436/88; 436/170
[58] Field of Search ............... 422/56–58; 435/805, 7.4, 970; 436/170, 66, 71, 88

[56] References Cited

U.S. PATENT DOCUMENTS

| | | | |
|---|---|---|---|
| 2,800,458 | 7/1957 | Green | 252/316 |
| 4,290,847 | 9/1981 | Johnson et al. | 176/1 |
| 4,356,149 | 10/1982 | Kitajima et al. | 422/56 |
| 4,438,067 | 3/1984 | Siddiqi | 422/56 |
| 4,732,849 | 3/1988 | Seshimoto et al. | 422/56 X |

FOREIGN PATENT DOCUMENTS

| | | |
|---|---|---|
| 0013156 | 7/1980 | European Pat. Off. |
| 0141648 | 5/1985 | European Pat. Off. |
| 3150102 | 7/1982 | Fed. Rep. of Germany |
| 3235658 | 4/1983 | Fed. Rep. of Germany |

OTHER PUBLICATIONS

Chemical Abstracts, vol. 107 (1987) p. 304; 107:214482k.
Chemical Abstracts, vol. 104 (1986) p. 110; 104:111771n.
63–Pharmaceuticals, vol. 104 (1986) p. 365; 104:56406v.

*Primary Examiner*—Jill A. Johnston
*Attorney, Agent, or Firm*—McAulay Fisher Nissen Goldberg & Kiel

[57] ABSTRACT

A dry multilayer analysis element which allows easy permeation of a high molecular weight component or hydrophobic component, which has, in order, at least a water permeable porous reagent layer, a water permeable light reflecting/screen layer, and a water permeable porous spreading layer on a water-impermeable transparent support, a reagent composition capable of producing an optically detectable substance in the presence of a component to be detected being incorporated in at least one of the water-permeable layers including said reagent layer, said light reflecting/screen layer being porous and comprised microcapsules having a core containing light reflective/screen grains and a shell made of a high molecular weight compound, wherein each of said reagent layer, spreading layer, and reflecting/screen layer allows permeation of a high molecular weight or hydrophobic component therethrough.

32 Claims, 1 Drawing Sheet

DRY LIQUID ANALYSIS ELEMENT

FIELD OF THE INVENTION

The present invention relates to a dry chemical analysis element for use in the determination of a specific substance in body fluids, such as, blood.

BACKGROUND OF THE INVENTION

The quantative analysis of various metabolic components present in body fluids, e.g., glucose, bilirubin, urea nitrogen, uric acid, cholesterol, lactic acid dehydrogenation enzyme, creatine kinase, glutamic oxaloacetic transaminase (GOT) and glutamic pyruvic transaminase (GPT) is clinically important and is indispensable to the diagnosis of diseases, checking of medical treatment, and monitoring of prognosis. In the clinicochemical examination of blood or the like as a specimen, it is desirable that an examination with high accuracy be effected using only a small amount of a liquid specimen. A wet analysis process using a reagent solution has heretofore been used. However, such wet analysis process lacks rapidity.

A dry chemical analysis, i.e., a clinical analysis method using an analyzing reagent system incorporated in a water-permeable carrier in a substantially dry analysis element, such as, a test piece or multilayer analysis element, has been known. The dry chemical analysis process is better than the wet analysis process in ease of use, minimization of the amount needed of a specimen to be tested and rapidity of analysis In other words, the use of a dry multilayer analysis element enables a highly precise, simple and rapid analysis of a small amount of a liquid specimen Such a dry multilayer analysis element is disclosed in JP-B-53-21677 (The term "JP-B" as used herein means an "examined Japanese patent publication"), and JP-A-55-164356, and 60-222769. (The term "JP-A" as used herein means an "unexamined published Japanese patent application". Patents written in English and corresponding to Japanese Patent Publications cited in this application are shown hereinafter.).

A typical dry multilayer analysis element consists of a transparent support, a reagent layer, a reflective layer and a spreading layer. The reagent layer coated on a water impermeable transparent support (e.g., undercoated plastic film) comprises a reagent which reacts with the component to be determined contained in the liquid specimen and which develops color at an optical density corresponding to the amount of the component. The reflective layer is adapted to prevent light incident to the reagent layer from reaching the spreading layer so that the optical measurement of the reagent layer is not affected by the liquid specimen spotted on the spreading layer. The spreading layer is adapted to spread the spotted liquid specimen over an area substantially proportional to the amount of the liquid specimen When such a dry analysis element is used for quantitative determination, a liquid specimen, such as, whole blood is spotted onto the surface of the spreading layer in a specified amount The blood, thus spread over the spreading layer, passes through the reflective layer and reaches the reagent layer where it reacts with a reagent to develop color. After the liquid specimen is dropped on the spreading layer, the analysis element is kept at a predetermined temperature for a proper period of time to allow the color development reaction to proceed. The optical reflection density of the reagent layer is determined from the support side at a specified wavelength range. The quantitative determination is conducted from the optical reflection density on the basis of a predetermined calibration curve.

As described in JP-A-58-70163, if the reagent layer composed of a hydrophilic high molecular weight compound such as gelatin is used, a component having high molecular weight, such as protein (e.g., albumin), various enzymes which also are proteins, polysaccharides, or a hydrophobic component, such as cholesterol, triglyceride and bilirubin, cannot diffuse into the reagent layer, making it impossible to react with the reagent. Thus, such a component cannot be detected.

As a means for solving such a problem an approach has been taken which comprises allowing a high molecular weight component or hydrophobic component to undergo reaction in the spreading layer In accordance with this approach, these components are allowed to undergo reaction in the spreading layer without being diffused into the reagent layer. In one form of this process, a dye produced in the reagent layer and/or spreading layer is diffused through light reflecting layer into a detection layer provided below the light reflecting layer (near the support), and is then detected in the detection layer. In another form, a low molecular weight intermediate produced by the reaction in the spreading layer is diffused into a color reagent layer provided below the spreading layer (near the support) where it is detected. However, the former process is disadvantageous in that since the proportion of a dye diffused into the detection layer is low, the analysis sensitivity is insufficient. The latter is disadvantageous in that it is susceptible to interference from interfering components in the sample liquid. Examples of the former process include a process which comprises detection of a dye produced in the spreading layer without diffusing it into other layers In this process, layers other than the spreading layer are omitted. However, this process is disadvantageous in that it is difficult to analyze whole blood because the background is variable.

In order to enable the detection of a high molecular weight component or hydrophobic component, a dry multilayer analysis element comprising a reagent layer made of a grain structure comprising bound polymer grains has been proposed in JP-A-55-90859 and 58-70163. However, such an improved reagent layer exhibits certain disadvantage. If a light reflecting layer or the like provided between the spreading layer and the reagent layer inhibits the diffusion of a high molecular weight component or a hydrophobic component, the analysis of these components is made difficult.

As a light reflecting layer of a dry multilayer analysis element, a layer comprising grains of inorganic material, such as, titanium oxide or barium sulfate dispersed therein with a hydrophilic high molecular weight compound as a binder is disclosed in U.S. Pat. Nos. 3,992,158 and 4,042,335 (JP-B-58-18628). In such a layer, if the proportion (volume or weight) of the binder is too high, the permeation of a high molecular weight component or a hydrophobic component therethrough is difficult to achieve. On the contrary, if the proportion of the binder is too low, the mechanical properties of the layer are poor though permeation of a high molecular weight component or a hydrophobic component through the layer is possible. The layer becomes extremely brittle and is subject to cracking that may cause separation of the grains.

SUMMARY OF THE INVENTION

It is therefore an object of the present invention to provide a dry multilayer analysis element comprising a light reflecting/screen layer which allows easy permeation of a high molecular weight component or a hydrophobic component and does not suffer from cracking or separation of grains.

(In the present invention "a light reflecting/screen" means "a function of light reflecting and/or a function of light screen".)

It is another object of the present invention to provide a dry multilayer analysis element comprising a light reflecting/screen layer which contains solid grains of a light reflecting material, such as titanium oxide, or light absorbing material such as carbon, but enables easy permeation of a high molecular weight component or a hydrophobic component and does not suffer from cracking or separation of the grains.

These and other objects of the present invention will become more apparent from the following detailed description and examples.

These objects of the present invention are accomplished with a dry multilayer analysis element which comprises a reagent layer, a light reflecting/screen layer, and a spreading layer in this order on a water-impermeable transparent support wherein all three layers on the support are water-permeable, and a reagent composition capable of producing an optically detectable substance in the presence of a component to be detected is incorporated in at least one of the water-permeable layers including said reagent layer, wherein the reagent layer and said spreading layer are porous and enable permeation of a high molecular weight or hydrophobic component and said light reflecting/screen layer is porous and comprised microcapsules comprising a core containing one or more light reflecting/absorbing grains and a shell made of a high molecular weight compound and allows permeation of a high molecular weight or a hydrophobic component.

DETAILED DESCRIPTION OF THE INVENTION

The analysis element of the present invention comprises at least a reagent layer, a light reflecting/screen layer and a spreading layer in this order disposed on a water-impermeable transparent support. These four layers, including the support, may be adjacent to each other or may have other water permeable layers interposed therebetween.

For example, a second reagent layer, a detection layer for receiving a dye or the like, and/or a water-absorbing layer for accelerating the permeation of an aqueous liquid specimen or the like may be provided between the support and the reagent layer. Into the detection layer, a dye or other detectable substance produced in the presence of a component to be detected is diffused and optically detected through the light transmitting support. The detection layer may be made of a hydrophilic polymer. The detection layer may comprise a mordant, such as cationic polymer with respect to anionic dye. The water-absorbing layer is normally a layer in which the dye produced in the presence of a component to be detected is prevented from substantially diffusing therein. The water-absorbing layer may be made of a swellable hydrophilic polymer, such as gelatin. The thickness of the water-absorbing layer is generally from 3 to 20 $\mu$m.

Also, a blood cell filter layer (as described in U.S. Pat. No. 3,992,158 (JP-B-53-21677), and JP-A-62-138756, 62-138757, and 62-138758), an interferent removing layer (as described in U.S Pat. No. 4,303,408 (JP-A-56-122956)) or the like may be provided between the spreading layer and the light reflecting/screen layer. Alternatively, an interferent removing layer may be provided between the light reflecting/screen layer and the reagent layer; or an interferent removing layer, a light reflecting layer (as described in U.S. Pat. No. 4,042,335) or the like may be provided between the detection layer and the reagent layer.

A suitable material for the water-impermeable transparent support is polyethylene terephthalate. Other examples of materials for the water-impermeable transparent support include cellulose esters, such as, cellulose triacetate. The support is normally provided with a subbing layer or subjected to a treatment to make the surface of the support hydrophilic so that a hydrophilic layer can be firmly adhered thereto.

The reagent composition is a composition capable of producing an optically detectable substance, such as, a dye in the presence of a component to be detected. Examples of such compositions include a composition (indicator) which reacts with a component to be detected or reacts with an intermediate produced by the reaction of a component to be detected and a reagent, producing an optically detectable substance such as a dye. Examples of such indicators include compositions containing a leuco dye which undergoes oxidation to produce a dye (e.g., arylimidazole leuco dye as described in U.S. Pat. No. 4,089,747, and JP-A-59-193352), diazonium salts, compositions containing a compound which undergoes oxidation and coupling with other compounds to produce a dye (e.g., 4-aminoantipyrines, phenols, naphthols), and compositions capable of producing a dye in the presence of a reducing coenzyme and an electron transferring agent. In the case of an analysis element for measuring enzymatic activity, a self-developable substrate capable of liberating a color substance, such as p-nitrophenol, may be incorporated in the reagent layer or spreading layer.

The reagent composition may be entirely incorporated in the porous reagent layer or may be partially incorporated in another porous or non-porous layer. For example, a composition which causes reaction of a component to be detected with a reagent to produce an intermediate may be incorporated in the reagent layer, and another composition (indicator) which reacts with the intermediate thus produced to form a dye may be incorporated in the second reagent layer provided between the reagent layer and the support. In this case, the second reagent layer may be a substantially uniform layer comprising a hydrophilic polymer as a binder. Suitable hydrophilic polymers for this use include gelatin, gelatin derivative (e.g., phthalated gelatin), cellulose derivative (e.g., hydroxypropyl cellulose), agarose, an acrylamide polymer, a methacrylamide polymer, or a copolymer of acrylamide or methacrylamide and various vinyl monomers. A gas-transmitting layer or an inhibiting interferent layer (as described in U.S. Pat. No. 4,066,403) may be provided between the first reagent layer and the second reagent layer. These layers may be water-impermeable if necessary.

A suitable reagent layer is a fibrous porous layer such as filter paper, woven or nonwoven fabric; a non-fibrous porous layer, including a blush polymer layer made of a cellulose ester as described in JP-B-53-21677 and U.S. Pat. No. 1,421,341, such as cellulose acetate, cellulose acetate/butyrate or cellulose nitrate; a microporous film made of a polyamide, such as 6-nylon or 6,6-nylon, a polyethylene or a polypropyrene; and microporous films made of a polysulfone as described in JP-A-62-27006. Preferred are the blush polymer and polysulfone microporous film. Alternatively, a porous layer having continuous voids comprising polymer grains, glass grains or diatomaceous earth bound with a hydrophilic or non-water-absorbent polymer as described in JP-B 53-21677 and JP-A-55-90859 or a polymer grain structure as described in JP-A-57-101760 and 57-101761.

In a membrane filter made of a so called blush polymer prepared by the phase separation process, the vertical liquid path is narrowest at the free surface (i.e., gloss surface) formed in the preparation of the film. If the reagent layer in the present analysis element comprises this kind of a film, the gloss surface of the membrane filter may preferably face the support.

The reagent composition can be substantially incorporated in the first non-fibrous porous layer by coating on a support a uniform layer containing a reagent composition with a hydrophilic polymer as a binder, followed by adhering a non-fibrous porous layer free of a reagent composition by a process as described in JP-A-55-164,356.

The reagent composition may optionally comprise an activator, a buffer, a film hardener, a surface active agent or the like. Examples of buffers which may be incorporated in the present analysis element include carbonate, borate, phosphate, and buffers as described in *Biochemistry*, Vol. 5, No. 2, pp. 467-477, 1988. These buffers may be selected in accordance with the description in Takekazu Horio et al., *Basic Experimental Process on Protein and Enzyme,* Nankodo, 1981 and Biochemistry, Vol. 5.

The reagent composition may comprise an enzyme. Reagent compositions as described in JP-A-62-138,756 to Nagatomo et al. (pp. 18-20) may be used.

An adhesion layer (subbing layer) on which a porous reagent layer can be adhered and laminated may be provided on the support, water-absorbing layer, detection layer or the like. Preferably, adhesion layer may be made of a hydrophilic polymer which swells with water to adhere to a porous layer, such as gelatin, a gelatin derivative, a polyacrylamide or starch.

The light reflecting/screen layer is adapted to screen the red color of hemoglobin in whole blood and serve as a light reflecting or background layer when reflection photometry is effected from the light transmitting support to determine a detectable change developed in the detection layer, reagent layer or the like (e.g., color change, color development). The analysis element of the present invention is characterized in that the light reflecting/screen layer comprises microcapsules comprising a shell comprising a hydrophilic or hydrophobic high molecular weight compound and a core comprising light reflecting/absorbing grains contained in the shell.

The core comprises light reflecting grains or light absorbing grains dispersed in an organic liquid. Examples of such an organic liquid include mineral oils, animal oils, vegetable oils and synthetic oils. Specific examples of mineral oils include petroleum, kerosine, naphtha and paraffin. Specific examples of animal oils include fish oil and lard. Specific examples of vegetable oils include peanut oil, linseed oil, soy bean oil, castor oil and corn oil. Specific examples of synthetic oils include biphenyl compound a(e.g., isopropyl biphenyl, isoamyl biphenyl), terphenyl compound, alkyl naphthalene (e.g., diisopropyl naphthalene), alkylated diphenyl alkane (e.g., 2,4-dimethyl diphenyl alkane), chlorinated paraffin, and phthalated ester (e.g., dibutyl phthalate, dioctyl phthalate).

White or bright pigments may be used as light reflecting grains to be dispersed in such an organic liquid. Preferred examples of such a pigment include titanium oxide, zinc oxide, lithopone, silica, alumina, barium sulfate, calcium sulfate, calcium carbonate, magnesium carbonate, kaolinite, haloisite, muscovite, and talc. Among these pigments, titanium oxide is most preferred.

The core of the microcapsules may comprise light absorbing grains dispersed in an organic liquid. Examples of such light absorbing grains include black pigments, such as, carbon black and black iron oxide. (In this case, the present light reflecting/screen layer is a light screen layer.)

These solid grains normally have an average particle diameter of 2 $\mu$m or less, particularly 0.02 to 1 $\mu$m. The volume ratio of solid grain to liquid is normally in the range of about 1:1 (substantially corresponding to closest packing) to 1:20. The organic liquid needs to contain solid grains in an amount such that it provides a sufficient light reflecting and/or screen effect. However, the amount of solid grains to be incorporated in the organic liquid preferably is limited to a value such that the surface of the solid grains are not exposed to the exterior of capsule grains. The organic liquid may contain an aid, such as a surface active agent, to maintain a dispersion of the solid grains, such as the pigment grains therein.

As a material for production of the shell of the microcapsules a high molecular weight compound which does not dissolve in the oil contained in the shell and in water is used.

The preferable material of the shell (or wall) of the microcapsules can be selected from the group consisting of proteins (e.g., collagen, gelatin, and casein), polypeptides, polyurethanes, polyureas, polyamides, polyesters, urea-formalin condensates, polystyrenes, polyethylenes, waxes, polyacrylamides, polyacrylic acids, polyvinyl alcohols, alginic acids, cellulose derivatives (e.g., methyl cellulose, ethyl cellulose, and carboxymethyl cellulose), gum arabic, and starch. The thickness of the shell of the microcapsules is normally in the range of from 0.01 to 6 $\mu$m. The static charge in the shell is not specifically limited. In other words, the shell may be positively or negatively charged or free of electric charge.

The microencapsulation process can be properly selected from various known methods, such as an interfacial polymerization process, an in situ process, a submerged hardening process, a coacervation process, a phase separation process, a submerged drying process, a fusion-dispersion-cooling process, a gas suspension process, a spray drying process and a static coalescence process. It is preferable that the microcapsules used in the present invention are produced by using a conden produced by using a condensation polymerization method. Examples of material produced by such a method include a polyurethane, a polyurea, a polyamide and a urea-formalin condensate.

As methods for encapsulation, there are known the methods described in U.S. Pat. Nos. 2,800,457 and 2,800,458, in which coacervation of hydrophilic colloid sol is utilized; interfacial polymerization method as described in British Patents 867,797, 950,443, 989,264 and 1,091.076, and so on; the technique described in U.S. Pat. No. 3,103,404; and so on.

In order to increase the viscosity of the organic liquid in the core so as to stably disperse the grains, the core of the microcapsules may comprise the above described high molecular weight compound as used in the shell of the microcapsules. The compound is a hydrophobic compound which can be dissolved in the organic liquid.

The shell of the microcapsules is preferably substantially free of light reflecting/screen solid grains because they tends to coalesce if the shell contains the solid grains. However, the shell of the microcapsules may comprise some of solid grains unless the stability of the microcapsules deteriorated.

The average particle diameter of the microcapsules is preferably in the range of 1 to 50 μm, more preferably 2 to 30 μm. When the diameter exceeds 100 μm, openings among the microcapsules in the light reflecting/screen layer become too large to prevent blood corpuscle pass through the holes. On the other hand, when the diameter is less than 1 μm passing through of a high molecular weight compound tends to be difficult.

The light reflecting/screen layer of the present invention should be substantially composed of the microcapsules in order to form a porous layer through which a high molecular weight component or a hydrophobic component can easily transmit.

The light reflecting/screen layer of the present invention may be formed by coating a composition wherein microcapsules are formed, directly onto a layer in the analysis element if the microcapsules can be adhered to each other to form a porous layer. Alternatively, the microcapsules are dispersed in a liquid dispersion medium, and then the dispersion thus obtained is subjected to coating on a layer. Generally, water is used as the dispersion medium. In order to stabilize the dispersibility of the microcapsules in the medium or in order to increase the viscosity of the coating composition, a water soluble high molecular weight compound is used as a binder in such an amount that permeation of a high molecular weight or hydrophobic analyte (substance to be detected) is not inhibited from transmitting openings among the microcapsules forming the light reflecting/screen layer. It is preferable that the layer has porosity ranging from 6 to 30%. The amount of the water-soluble high molecular weight compound in the layer is preferably from 0.5 to 15% by volume based on the apparent volume of the layer.

The thickness of the light reflecting/screen layer is generally from 20 to 200 μm, and the amount of the light reflective/screen grains is preferably from 25 to 75% by volume based on the apparent volume of the layer. The number of the microcapsules in the direction of the layer thickness is preferably 5 to 100.

Examples of such a water soluble high molecular weight compound include methyl cellulose, hydroxypropylmethyl cellulose, hydroxypropyl cellulose, gelatin, acylated gelatin such as phthalated gelatin, poly(vinylpyrolidone), poly(vinylalcohol), poly(acrylamide), and the like.

The microcapsules used in the present invention preferably can withstand a pressure of at least 30 kg/cm$^2$ applied perpendicular to the surface of the analysis element, without destruction of the microcapsule wall.

The spreading layer is preferably a layer having metering effect on specimen liquid. This liquid metering effect is to spread the specimen liquid dropped on the spreading layer, in the surface direction at a substantially constant rate per unit area thereof without unevenly distributing the components of the liquid. Suitable for use as a fibrous porous material for the spreading layer are filter paper, nonwoven fabric, fabric (e.g., plain weave fabric), knit fabric (e.g., tricot), or glass fiber filter paper. Among these materials fabric and knit fabric are preferred. The fabric may be subjected to glow discharge as described in JP-A-57-66,359. The spreading layer may contain a hydrophilic high molecular weight compound or surface active agent as described in JP-A-60-222770, 63-219397, 63-112,999, and 62-182652 to adjust the developing area, developing speed or the like. The spreading layer may be a non-fibrous spreading layer as described in U.S. Pat. No. 3,992,158.

The dry analysis element of the present invention enables a rapid determination of high molecular weight components such as total protein, albumin and various enzymes, components bonded to protein, such as bilirubin, and hydrophobic components, such as cholesterol and glyceride, as well as low molecular weight component, such as glucose, urea and uric acid in whole blood at a high sensitivity.

The layers of the analysis element of the present invention are not subject to brittleness which results in cracking of the light reflecting/screen layer, scatter or falling-off of grains noted above, which occurs in the layers as described in U.S. Pat. Nos. 3,992,158 and 4,042,335 (JP-B-58-18628), consisting of grains of inorganic substance such as titanium oxide and barium sulfate, dispersed therein with a hydrophilic high molecular weight compound as a binder wherein the proportion of the binder is low enough to enable the permeation of a high molecular weight compound or hydrophobic component.

The dry analysis element of the present invention can be used for the immunological determination of an antigen or antibody if the porous layer contains at least one of the antigen and antibody.

Figure 1:
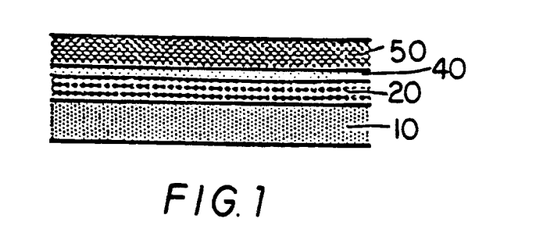
FIG. 1 shows a section of a multilayer analysis element of Example 1.
Figure 2:
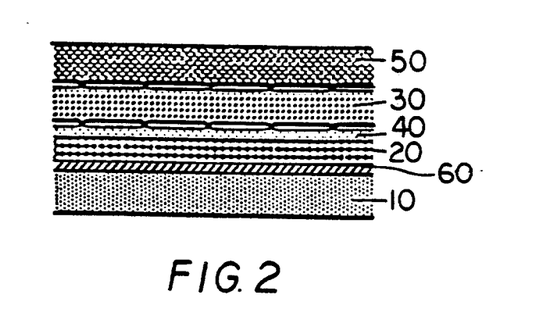
FIG. 2 shows a section of a multilayer analysis element of Example 2.

Two embodiments of the present invention are depicted in FIGS. 1 and 2, respectively, wherein 10 indicates the support layer, 20 indicates the reagent layer, 30 indicates the filtering layer, 40 indicates the light reflecting/screen layer, 50 indicates the spreading t layer, and 60 indicates the water-absorbing layer.

The present invention will be further described in the following examples, but should not be construed as being limited thereto.

EXAMPLE 1

1) Preparation of microcapsules 8 g of a methacrylic ester/acrylic acid copolymer (molecular weight: 100,000) was dissolved in 12 g of monoisobutyl diphenylethane at a temperature of 80° C. 15 g of powdered titanium oxide (PF656; manufactured by Ishihara Sangyo K.K. (average particle diameter: 0.2 μm)) was added to the solution. The admixture was then subjected to a dispersion treatment in an electric mortar for 8 hours. The following mixture was admixed with the dispersion by stirring with a glass rod.

| Methacrylic ester/acrylic acid copolymer* (molecular weight: about 100,000) | 12 g |
| Ethyl acetate | 18.5 g |
| Paraffin oil (average number of carbon atoms: 12) | 12 g |

*Acrylbase MM2002-2 (manufactured by Fujikura Kasei)

The following mixture was then added to the system. The system was thoroughly stirred with a glass rod to give Liquid I.

| Ethyl acetate | 14 g |
| Silicone oil (KF96 1000: product manufactured by Shinetsu Chemical Industry Co., Ltd.) (used as a lubricant) | 4 g |
| 1,1,1-Tri(p-isocyanatomethylbenzyl-aminocarbonyloxymethyl)propane (shell-forming substance) | 28 g |

10 g of a 2.5% aqueous solution of diethylenetriamine was added to 180 g of a 4% aqueous solution of methyl cellulose (protective colloid). Liquid I was then added to the admixture with stirring so that it was dispersed. The dispersion was accomplished by means of Matsushita Electric Industrial Co., Ltd.'s Cooking Mixer MX915C'. A voltage adjuster was used to adjust the voltage to 40 V. In operation, the system was stirred at a mayonnaise mode (low speed) for 20 seconds. The system was then subjected to dispersion at a grinding mode (high speed) at 100 V for 3 minutes 30 seconds.

64 g of a 5% aqueous solution of diethylenetriamine was then added to the dispersion and diethylenetriamine was reacted with the above-described isocyanate compound at a temperature of 60° C. for 3 hours. After the reaction was completed, the reaction product was washed with water, and then dried to obtain microcapsules (II).

2) Preparation of analysis element

The following composition (a) was coated on a 180-μm thick gelatin-coated colorless transparent plain polyethylene terephthalate film as an aqueous solution and dried to form a reagent layer.

| (a) | |
|---|---|
| Gelatin | 1.2 g/m² |
| Particulate polyolefin (Chemipearl M200; product manufactured by Mitsui Petrochemical Industries, Ltd. particle diameter: 5 μm; density: 0.92) | 41 g/m² |
| Surface active agent (Polyoxyethylene nonylphenyl ether) | 0.22 g/m² |
| Trishydroxymethylaminomethane | 0.32 g/m² |
| Monopotassium phosphate | 0.32 g/m² |
| α-Ketoglutaric acid | 0.1 g/m² |
| Sodium L-asparaginate | 0.5 g/m² |
| Decarboxylase oxaloacetate | 2,520 IU/m² |
| Flavin adenine dinucleotide (FAD) | 6 mg/m² |
| Thiamine pyrophosphate (TPP) | 24 mg/m² |
| Oxidase pyruvate | 7,000 IU/m² |
| Peroxidase | 1,280 IU/m² |
| Dye: 2-(3,5-Dimethoxy-4-hydroxy phenyl)-4-phenethyl-5-(4-dimethylaminophenyl)imidazole (added as 5% methanol solution) | 0.36 g/m² |
| H₂O | 100 ml/m² |

(The pH value of the composition was adjusted to 7.5 with dilute NaOH solution.)

The following composition (b) was coated on the thus formed reagent layer as a solution and dried to form a light reflecting/screen layer.

| (b) | |
|---|---|
| Microcapsules (II) | 39 g/m² |
| Methyl cellulose | 2 g/m² |

(65SH50: product manufactured by Shinetsu Chemical Industry Co., Ltd. containing ca. 10 mol% of hydroxypropyl cellulose)

| H₂O (solvent) | 50 ml/m² |

A starch paste was adhered to the surface of a polyester tricot (thickness: 0.25 mm; void volume: about 18 μl/cm²) by a screen printing process through a 100-mesh screen. The tricot was then laminated on the microcapsule layer to prepare an AST (aminotransphellase) asparaginic acid) activity measuring integrated multilayer analysis element (FIG. 1).

COMPARATIVE EXAMPLE 1

An integrated multilayer analysis element for AST activity measurement was prepared in the same manner as in Example 1 except that the composition (b) was replaced by the following composition (c):

| (c) | |
|---|---|
| Deionized gelatin | 11 g/m² |
| Surface active agent (polyoxyethylene nonylphenyl ether) n = 40 (polymerization degree of ethyleneoxide) | 0.4 g/m² |
| Rutile titanium oxide (R780: product manufactured by Ishihara Sangyo K.K.) | 18 g/m² |
| H₂O (solvent for coating) | 40 ml/m² |

(The pH value of the composition was adjusted with dilute NaOH solution to 7.5.)

Measurement Example 1

10 μl of controlling serums having different AST activity values (obtained by adding necessary amounts of SIGMA-made pig-derived AST to Dade-made Moni-Trol I) as shown in Table 1 were dropped on the analysis elements prepared in Example 1 and Comparative Example 1. These analysis elements were then stored at a temperature of 37° C. in a sealed container. These analysis elements were then measured for reflective density at a wavelength of 640 nm after storing for 4 minutes and 6 minutes. The change in the reflective density per 1 minute was then determined from these measurements. AST activity was then calculated from this change in the reflective density and a calibration curve which had been previously prepared (the activity of the standard solution was calibrated by wet method using Hitachi 7050 chemical analyzer). The results are shown in Table 1.

TABLE 1

| Actual Concentration | Example 1 | Comparative Example 1 |
|---|---|---|
| 105 unit/l | 101 unit/l | Unmeasurable |
| 420 | 452 | Unmeasurable |

TABLE 1-continued

| Actual Concentration | Example 1 | Comparative Example 1 |
|---|---|---|
| 863 | 876 | Unmeasurable |

In Comparative Example 1, the color density was low, and AST activity could not be measured. On the contrary, in Example 1, AST activity was measured with the excellent accuracy as shown in Table 1.

EXAMPLE 2

An aqueous solution of gelatin was coated on a 180-μm thick gelatin-coated colorless transparent polyethylene terephthalate film having a smooth surface to a dried film thickness of 7 μm, and then dried to prepare a water-absorbing layer.

The surface of the water-absorbing layer thus prepared was substantially uniformly wet with water of about 25° C. A cellulose acetate membrane filter having a maximum pore diameter of 3 μm, a thickness of 140 μm and a void volume of about 80% (Microfilter FM300: product manufactured by Fuji Photo Film Co., Ltd.) was then laminated on the water-absorbing layer. The lamination was dried so that the membrane filter was adhered to the water-absorbing layer.

The following compositions 1 and 2 were then coated on the membrane filter in sequence in amounts shown below. The lamination was dried to obtain a porous reagent layer.

| Composition 1: | |
|---|---|
| Gelatin | 0.64 g/m$^2$ |
| Surface active agent (polyoxyethylene nonylphenyl ether) | 2.5 g/m$^2$ |
| Trishydroxymethylaminomethane | 0.46 g/m$^2$ |
| Monopotassium phosphate | 0.46 g/m$^2$ |
| α-Ketoglutaric acid | 0.5 g/m$^2$ |
| sodium L-asparaginate | 2.5 g/m$^2$ |
| Decarboxylase oxaloacetate | 12,600 IU/m$^2$ |
| Magnesium chloride (anhydride) | 0.3 g/m$^2$ |
| FAD | 28 mg/m$^2$ |
| Thiaminepyrophosphoric acid | 118 mg/m$^2$ |
| Oxidase pyruvate | 35,000 IU/m$^2$ |
| Peroxidase | 6,400 IU/m$^2$ |
| Solvent: water | 100 ml/m$^2$ |

The pH value of the composition was adjusted with dilute NaOH solution to 7.5.)

| Composition 2: | |
|---|---|
| Leuco dye: 2-(3,5-Dimethoxy-4-hydroxyphenyl)-4-phenethyl-5-(4-dimethylaminophenyl)imidazole | 1.8 g/m$^2$ |
| Surface active agent (polyoxyethylene (n = 40) nonylphenyl ether) | 0.6 g/m$^2$ |
| Solvent: ethanol | 120 ml/m$^2$ |

A mixture of the microcapsules (II) prepared in Example 1 and methyl cellulose was coated on the porous reagent layer above in the following coating amount. Thus, a light reflecting/screen layer was provided on the membrane filter.

| Microcapsule (II) | 20 g/m$^2$ |
|---|---|
| Methyl cellulose (65SH50: manufactured by The Shinetsu Chemical Industry Co., Ltd.) | 4 g/m$^2$ |
| H$_2$O | 100 ml/m$^2$ |

A starch paste was adhered to the surface of Microfilter FM300 (product manufactured by Fuji Photo Film Co., Ltd.), a cellulose acetate membrane filter having a minimum pore diameter of 3.0 μm, a thickness of 140 μm and a void volume of about 80%, in an amount of 3 g/m$^2$ in terms of solid content by a screen printing process through a 100-mesh net (areal density: about 20%). This microfilter was then laminated on the membrane filter and dried to form a blood cell filter layer.

A tricot having a thickness of about 250 μm made of PET cotton yarn having 100S was adhered and integrated to the second non-fibrous porous layer by the same net adhesion process as described above to prepare an AST activity measuring analysis element (FIG. 2).

COMPARATIVE EXAMPLE 2

An analysis element was prepared in the same manner as in Example 2 except that the light reflecting/screen layer comprising microcapsules was omitted and a blood cell filter layer was directly laminated on a porous reagent layer.

REFERENCE EXAMPLE

In order to examine the light screening effect of the light reflecting/screen layers prepared in Example 2 and Comparative Example 2, the following measurements were conducted.

i. The blood cell filter layer and above layers were peeled off the analysis element so that the light reflecting/screen layer and under layers were left.
 ii. The analysis element remaining was soaked with water.
 iii. The reflection by the analysis element was measured at the support side. In this measurement, the optical density was determined when a black board and a white board, respectively, were placed in the background.

TABLE 2

| Wavelength | Background | Example 2 | Comparative Example 2 |
|---|---|---|---|
| 540 nm | White | 0.250 | 0.480 |
| | Black | 0.260 | 0.730 |
| 600 nm | White | 0.210 | 0.420 |
| | Black | 0.230 | 0.680 |
| 650 nm | White | 0.200 | 0.390 |
| | Black | 0.230 | 0.690 |

Table 2 shows that Example 2 exhibits an optical density difference of 0.01 to 0.03 while Comparative Example 2 exhibits an optical density difference of 0.25 to 0.3 between the white background and the black background. Thus, the optical density difference was reduced to 1/10 or less.

It was then confirmed whether the light reflecting/screen layer allows the passage of a high molecular weight compound. The following method was employed.

10 mg of BLUE DEXTRAN (Catalogue No. D-5751; molecular weight: about 2,000,000) available from SIGMA Corp. was dissolved in 1 ml of water. 10 μl of the solution was dropped onto the analysis element prepared in Example 2. After 10 seconds, a blue light was observed from the support side.

MEASUREMENT EXAMPLE 2

An AST derived from pig (SIGMA Corp.) was added to blood plasma (hematocrit value: 0%) and a fresh blood having a hemacrit value of 30% (drawn with heparin) in amounts such that the AST activity thereof reached 320 unit/l and 790 unit/l. Thus, four types of blood were prepared. The analysis element prepared in Example 2 was cut into pieces of 1.5 cm × 1.5 cm. These pieces were then inserted into a plastic mount provided with holes for spotting a specimen onto the element and for optical measurement, respectively. The four types of blood were applied in droplets to these pieces. After application, the reaction system was allowed to undergo reaction at a temperature of 37° C. Reflectmetry was then conducted at the support side to determine the absorption of 640 nm after 2.5 minutes and after 4 minutes. These absorptivity values were converted to ODt (transmission optical density) in accordance with the principle described in Clinical Chemistry, Vol. 24, 1335 (1978). These ODt values were then used to calculate AST activity values. The results are shown in Table 3.

TABLE 3

|  | Hemacrit value | |
| --- | --- | --- |
|  | 0% (blood plasma) | 30% |
| 320 unit/l | 330 | 310 |
| 795 | 810 | 792 |

Table 3 shows that the analysis element of their present example exhibits little difference in AST activity value between fresh blood and blood plasma.

EXAMPLE 3

An aqueous solution of gelatin was coated on a 180-μm thick gelatin-coated colorless transparent polyethylene terephthalate film having a smooth surface in an amount such that the dried film thickness reached 7 μm, and dried to form a water-absorbing layer.

The surface of the water-absorbing layer thus prepared was substantially uniformly wet with water of about 25° C. A cellulose acetate membrane filter having a minimum pore diameter of 1.2 μm, a thickness of 140 μm, and a void volume of about 80% (Fuji Photo Film Co., Ltd's Microfilter FM120) was then laminated on the water-absorbing layer. The lamination was dried so that the membrane filter was integrated to the water-absorbing layer.

The following compositions 1 and 2 were then coated on the membrane filter in sequence in amounts such that the coated amount of each component reached the values shown below. The lamination was dried to obtain a porous reagent layer.

| Composition 1: | |
| --- | --- |
| Leuco dye: 2-(3,5-Dimethoxy-4-hydroxyphenyl)-4-phenethyl-5-(4-dimethylaminophenyl)imidazole | 1.36 g/m² |
| Surface active agent (polyoxyethylene (n = 40) nonylphenyl ether) | 0.43 g/m² |
| Solvent: ethanol | 120 ml/m² |
| Composition 2: | |
| Gelatin | 2.13 g/m² |
| Polyoxyethylene nonyl phenyl ether: | |
| Oxyethylene unit 10 | 2.13 g/m² |
| Oxyethylene unit 40 | 0.13 g/m² |
| Cholesterol esterase | 8,070 unit/m² |
| Cholesterol oxidase | 88,500 unit/m² |
| Peroxidase | 28,200 unit/m² |
| H₂O (solvent) | 100 ml/m² |

A mixture of the microcapsules (II) prepared in Example 1 and methyl cellulose was coated on the porous reagent layer in an amount such that the composition proportion reached the following values. Thus, a light reflecting/screen layer was provided on the membrane filter.

| Microcapsule (II) | 48 g/m² |
| --- | --- |
| Methyl cellulose (65SH50: product manufactured by The Shinetsu Chemical Industry Co., Ltd.) | 4.1 g/m² |
| Polyoxyethylene nonyl phenyl ether (Oxyethylene unit 40) | 0.11 g/m² |
| H₂O (solvent) | 100 ml/m² |

A starch paste was adhered to the surface of Microfilter FM300 (product manufactured by Fuji Photo Film Co., Ltd.) (cellulose acetate membrane filter having a minimum pore diameter of 3.0 μm, a thickness of 140 μm and a void volume of about 80%) in an amount of 3 g/m² in terms of solid content by a screen printing process through a 100-mesh net (area density: about 20%). This microfilter was then laminated on the membrane filter and dried to form a blood cell filter layer.

A tricot having a thickness of about 250 μm made of polyethylene terephthalate cotton yarn having 100S was adhered and integrated to the 2nd non-fibrous porous layer by the same net adhesion process as described above to prepare a total cholesterol dry analysis element.

MEASUREMENT EXAMPLE 3

Blood cells separated from human whole blood (drawn through a heparin tube) were added to Dade-made controlling serum Moni-Trol I to prepare an artificial blood (I) with a hemacrit value of 40% and a total cholesterol value of 115 mg/m². The same blood cells as described above were added to Lipid Serum II manufactured by K. K. Eiken Kagaku to prepare an artificial blood (II) with a hemacrit value of 40% and a total cholesterol value of 351 mg/l.

The artificial serums (I) and (II) were each applied onto a dry analysis element prepared in Example 3 in amounts of 10 μl. The analysis elements were then stored at a temperature of 37° C. in a sealed container for 4 minutes. Each analysis element was then measured for reflective density at a wavelength of 640 nm.

TABLE 4

| Specimen | Calculated value | Measured value |
| --- | --- | --- |
| (I) | 115 mg/dl | 105 mg/dl |
| (II) | 351 | 348 |

Table 4 shows that the dry analysis element can be measured for total cholesterol with an excellent accuracy.

EXAMPLE 4

1) Preparation of microcapsules 18 g of powdered titanium oxide (PF656: product manufactured by Ishihara Sangyo K.K.; average particle diameter: 0.2 μm) was added to 27 g of diisopropyl naphthalene. The admixture was then subjected to a dispersion treatment in an electric mortar for 8 hours. A solvent mixture of 2.5 g of acetone and 7.5 g of methylene chloride was added to the dispersion. The dispersion was then thoroughly stirred to prepare a primary solution A 3 mol:1 mol addition product of hexamethylene diisocyanate and hexane triol was added to the primary solution to prepare a secondary solution.

The mixing dissolving of these materials was effected at a temperature of 25° C. or lower. The secondary solution thus prepared was then gradually added with vigorous stirring to a solution obtained by dissolving 3 g of gum arabic in 57 g of water at a temperature of 20° C., to obtain an oil in-water type emulsion having an oil drop diameter of 5 to 15 μm. In the preparation of the emulsion, the environment of the reaction container was cooled so that the temperature of the reaction system did not exceed 20° C.

100 g of water of 40° C. was further added to the emulsion with stirring while the temperature of the system was gradually increased. The temperature of the system reached 90° C. in 30 minutes and then was maintained at this value for 20 minutes. The system was then subjected to centrifugal separation so that the microcapsule portion was separated from the gum arabic solution. 100 g of water was then added to the microcapsule portion to finish desired microcapsules.

2) Preparation of analysis element

An AST activity measuring multilayer analysis element was prepared in the same manner as in Example 1 except that the microcapsules (II) were replaced by the above described microcapsules.

The analysis element thus prepared could be used to measure AST activity with an excellent accuracy similar to that obtained in Example 1.

Patents written in English and corresponding to Japanese Patent Publications referred hereinabove are listed below.
JP-B-53-21677 : U.S. Pat. No. 3,992,158
JP-A-55-164356 : U.S. Pat. No 4,292,272
JP-A-60-222769 : EP 0162302A
JP-A-58-70163 : U.S. Pat. No. 4,486,537
JP-A-55-90859 : U.S. Pat. No. 4,258,001; U.S. Pat. No. 4,357,363, U.S. Pat. No. 4,381,921
JP-A-57-101761 : U.S. Pat. No. 4,430,436
JP-A-60-222770 : EP 0162301A While the invention has been described in detail and with reference to specific embodiments thereof, it will be apparent to one skilled in the art that various changes and modifications can be made therein without departing from the spirit and scope thereof.

What is claimed is:

1. In a dry multilayer analysis element having, in order, at least a water permeable porous reagent layer, a water permeable light reflecting/screen layer, and a water permeable porous spreading layer on a water-impermeable transparent support, a reagent composition capable of producing an optically detectable substance in the presence of a component to be detected being incorporated in at least one of said water-permeable layers including said reagent layer, the improvement which comprises said light reflecting/screen layer being porous and comprised of microcapsules having a core containing light reflective/screen grains dispersed in an oil containing substantially no reagent and a shell made of a high molecular weight compound, wherein each of said reagent layer, spreading layer, and reflecting/screen layer allows permeation of a high molecular weight or hydrophobic component therethrough.

2. The analysis element of claim 1, wherein said microcapsules comprise a shell made of a hydrophilic high molecular weight compound.

3. The analysis element of claim 1, wherein said microcapsules comprises a shell made of a hydrophobic high molecular weight compound.

4. The analysis element of claim 1, wherein said high molecular weight compound is a compound selected from the group consisting of proteins, polypeptides, polyurethanes, polyureas, polyamides, polyesters, urea-formalin condensates, polystyrenes, polyethylenes, waxes, polyacrylamides, polyacrylic acids, polyvinyl alcohols, alginic acids, cellulose derivatives, gum arabic, and starch.

5. The analysis element of claim 2, wherein said hydrophilic high molecular weight compound is a compound selected from the group consisting of proteins, polypeptides, polyacrylamides, polyacrylic acids, polyvinyl alchols, alginic acids, hydrophilic cellulose derivatives, gum arabic and starch.

6. The analysis element of claim 3, wherein said hydrophobic high molecular weight compound is a compound selected from the group consisting of polyurethanes, polyureas, polyamides, polyesters, urea-formalin condensates, polystyrenes, polyethylenes, waxes and hydrophobic cellulose derivatives.

7. The analysis element of claim 1, wherein said light reflecting/screen grains comprises a pigment 8. The analysis element of claim 1, wherein the grains have an average particle diameter of not more than 2 μm.

9. The analysis element of claim 8, wherein the average particle diameter is at least 0.02 μm.

10. The analysis element of claim 1, wherein said light reflecting/screen grains comprise at least one pigment selected from the group consisting of titanium oxide, zinc oxide, lithopone, silica, alumina, barium sulfate, calcium sulfate, calcium carbonate, magnesium carbonate, kaolinite, haloisite, muscovite, talc, carbon black and black iron.

11. The analysis element of claim 1, wherein said light reflecting/screen grains comprise titanium oxide.

12. The analysis element of claim 1, wherein the volume ratio of grains to oil is in the range from about 1:1 to 1:20.

13. The analysis element of claim 1, wherein the average particle diameter of the microcapsules is in the range of from 1 to 50 μm.

14. The analysis element of claim 1, wherein said shell being substantially free from the grains.

15. The analysis element of claim 1, wherein the microcapsules forms a layer using a binder.

16. The analysis element of claim 15, wherein the binder is a water-soluble high molecular weight compound.

17. The analysis element of claim 1, wherein the element further comprises a water absorbing layer provided between the support and the reagent layer.

18. The analysis element of claim 1, wherein the element further comprises a filtering layer provided between the spreading layer and the light reflecting/screen layer.

19. The analysis element of claim 1, wherein the element further comprises an absorbing layer provided between the support and the reagent layer and a filtering, layer provided between the spreading layer and the light reflecting/screen layer.

20. The analysis element of claim 1, wherein the light reflecting/screen layer has porosity ranging from 6 to 30%.

21. The analysis element of claim 1, wherein the light reflecting/screen layer contains a binder in an amount of from 0.5 to 15% by volume based on the apparent volume of the layer.

22. The analysis element of claim 1, wherein the light reflecting/screen layer has a thickness of from 20 to 200 μm.

23. The analysis element of claim 1, wherein the light reflecting/screen layer contains the light reflective/screen grains in an amount of from 25 to 75% by volume based on the apparent volume of the layer.

24. The analysis element of claim 1, wherein the number of the microcapsules in the direction of the layer thickness is 5 to 100.

25. The analysis element of claim 1 wherein the core contains grains dispersed in an oil, the light reflecting/screen layer contains grains in an amount of from about 25 to 75% by volume based on the apparent volume of the layer and the number of microcapsules in the direction of the layer thickness is from 5 to 100.

26. The analysis element of claim 1 wherein said oil is selected from the group consisting of petroleum, kerosene, naphtha, paraffin, fish oil, lard, peanut oil, linseed oil, soy bean oil, castor oil, corn oil, biphenyl compound, terphenyl compound, alkyl naphthalene, alkylated diphenyl alkane, chlorinated paraffin, phthalated ester, and silicone oil.

27. In a method for the quantitative analysis of a liquid specimen wherein a specimen is spotted on a dry analysis element composed of layers adapted for the colorimetric analysis of the component in said specimen, and the optical density of a coloration formed is measured, the improvement which comprises the analysis element have, in this order, at least a water permeable porous reagent layer, a water permeable light reflecting/screen layer, and a water permeable porous spreading layer on a water-impermeable transparent support, and a reagent composition capable of producing an optically detectable substance in the presence of a component to be detected is incorporated in at least one of the water-permeable layers including said reagent layer, the improvement which comprises said light reflecting/screen layer being porous and comprised microcapsules having a core containing light reflective/screen grains dispersed in an oil containing substantially no reagent and a shell made of a high molecular weight compound, wherein each of said reagent layer, spreading layer, and reflecting/screen layer allows permeation of a high molecular weight or hydrophobic component therethrough.

28. The method for the quantitative analysis of claim 27, wherein said liquid specimen is a body fluids.

29. The method for the quantitative analysis of claim 27, wherein said liquid specimen is whole blood, blood plasma or serum.

30. The method for the quantitative analysis of claim 27, wherein said liquid specimen is whole blood.

31. The method for the quantitative analysis of claim 27, wherein said component is selected from the group consisting of albumin, enzymes, bilirubin, cholesterol and glyceride.

32. The method of claim 27 wherein the core contains grains dispersed in an oil, the light reflecting/screen layer contains grains in an amount of from about 25 to 75% by volume based on the apparent volume of the layer and the number of microcapsules in the direction of the layer thickness is from 5 to 100.

* * * * *